United States Patent [19]
Jaworski et al.

[11] Patent Number: 6,124,119
[45] Date of Patent: Sep. 26, 2000

[54] MECB

[75] Inventors: Deborah Jaworski, West Chester, Pa.; Elizabeth Lawlor, Sleaford, United Kingdom; Martin Rosenberg, Royersford, Pa.; Lisa Kathleen Shilling, Newtown, Pa.; Min Wang, Blue Bell, Pa.; Judith Ward, Dorking, United Kingdom; Martin Karl Russel Burnham, Norristown, Pa.; Andrew Fosberry, Linton, United Kingdom; John Hodgson, Romainville, France

[73] Assignees: SmithKline Beecham Corporation, Philadelphia, Pa.; SmithKline Beecham plc, United Kingdom

[21] Appl. No.: 09/040,843

[22] Filed: Mar. 18, 1998

Related U.S. Application Data

[60] Provisional application No. 60/057,535, Sep. 4, 1997.

[51] Int. Cl.⁷ .......................... C12P 21/06; C12N 15/00; C12N 5/00; C12N 1/20; C07H 21/04
[52] U.S. Cl. ................... 435/69.1; 435/320.1; 435/325; 435/252.3; 536/23.7
[58] Field of Search ............................... 435/69.1, 320.1, 435/325, 252.3; 536/23.7, 23.1

[56] References Cited

FOREIGN PATENT DOCUMENTS 0786519  7/1997  European Pat. Off. .
786-519 A2  7/1997  European Pat. Off. .

OTHER PUBLICATIONS

Min Dong Song: "Studies on the expression Mechanism of Beta–Lactam resistance in staphylococcus aureus" *Korean Biochemical Journal*, vol. 25, No. 4, 1992, pp. 342–346.

Corinne Rouquette, et al: "Identification of a ClpC ATPase required for stress tolerance and in vivo survival of Listeria monocytogenes" *Molecular Biology*, vol. 21, No. 5, Sep. 1996, pp. 977–987.

Tarek Msadek, et al: "MecB of *Bacillus subtilis*, a member of the ClpC ATPase family, is a pleiotropic regulator controlling competence gene expression and growth at high temperature" *Proceedings of the National Academy of Sciences of USA*, vol. 91, No. 13, Jun. 21, 1994, pp. 5788–5792.

EP search report from corresponding European patent application No. 98306683.8.

SwissProt Submission, Accession No. P37571, Direct Submission.

*Primary Examiner*—Bruce R. Campell
*Attorney, Agent, or Firm*—Edward R. Gimmi; William T. King; Thomas S. Deibert

[57] ABSTRACT

The invention provides mecB polypeptides and polynucleotides encoding mecB polypeptides and methods for producing such polypeptides by recombinant techniques. Also provided are methods for utilizing mecB polypeptides to screen for antibacterial compounds.

29 Claims, No Drawings

MECB

RELATED APPLICATIONS

This application claims benefit of U.S. Provisional Patent Application Ser. No. 60/057,535, filed Sep. 4, 1997.

FIELD OF THE INVENTION

This invention relates to newly identified polynucleotides and polypeptides, and their production and uses, as well as their variants, agonists and antagonists, and their uses. In particular, the invention relates to novel polynucleotides and polypeptides of the ClpC ATPase family, hereinafter referred to as "mecB".

BACKGROUND OF THE INVENTION

It is particularly preferred to employ Staphylococcal genes and gene products as targets for the development of antibiotics. The Staphylococci make up a medically important genera of microbes. They are known to produce two types of disease, invasive and toxigenic. Invasive infections are characterized generally by abscess formation effecting both skin surfaces and deep tissues. S. aureus is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

The frequency of Staphylococcus aureus infections has risen dramatically in the past few decades. This has been attributed to the emergence of multiply antibiotic resistant strains and an increasing population of people with weakened immune systems. It is no longer uncommon to isolate Staphylococcus aureus strains which are resistant to some or all of the standard antibiotics. This phenomenon has created a demand for both new anti-microbial agents, vaccines, and diagnostic tests for this organism.

Clearly, there exists a need for factors, such as the mecB embodiments of the invention, that have a present benefit of being useful to screen compounds for antibiotic activity. Such factors are also useful to determine their role in pathogenesis of infection, dysfunction and disease. There is also a need for identification and characterization of such factors and their antagonists and agonists to find ways to prevent, ameliorate or correct such infection, dysfunction and disease.

Certain of the polypeptides of the invention possess amino acid sequence homology to a known ClpC protein.

SUMMARY OF THE INVENTION

It is an object of the invention to provide polypeptides that have been identified as novel mecB polypeptides by homology between the amino acid sequence set out in Table 1 [SEQ ID NO: 2 or 4] and a known amino acid sequence or sequences of other proteins such as ClpC protein.

It is a further object of the invention to provide polynucleotides that encode mecB polypeptides, particularly polynucleotides that encode the polypeptide herein designated mecB.

In a particularly preferred embodiment of the invention the polynucleotide comprises a region encoding mecB polypeptides comprising a sequence set out in Table 1 [SEQ ID NO: 1 or 3] which includes a full length gene, or a variant thereof.

In another particularly preferred embodiment of the invention there is a novel mecB protein from Staphylococcus aureus comprising the amino acid sequence of Table 1 [SEQ ID NO:2 or 4], or a variant thereof.

A further aspect of the invention there are provided isolated nucleic acid molecules encoding mecB, particularly Staphylococcus aureus mecB, including mRNAs, cDNAs, genomic DNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of mecB and polypeptides encoded thereby.

Another aspect of the invention there are provided novel polypeptides of Staphylococcus aureus referred to herein as mecB as well as biologically, diagnostically, prophylactically, clinically or therapeutically useful variants thereof, and compositions comprising the same.

Among the particularly preferred embodiments of the invention are variants of mecB polypeptide encoded by naturally occurring alleles of the mecB gene.

In a preferred embodiment of the invention there are provided methods for producing the aforementioned mecB polypeptides.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing mecB expression, treating disease, assaying genetic variation, and administering a mecB polypeptide or polynucleotide to an organism to raise an immunological response against a bacteria, especially a Staphylococcus aureus bacteria.

In accordance with certain preferred embodiments of this and other aspects of the invention there are provided polynucleotides that hybridize to mecB polynucleotide sequences, particularly under stringent conditions.

In certain preferred embodiments of the invention there are provided antibodies against mecB polypeptides.

In other embodiments of the invention there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypeptide or polynucleotide by detecting the presence or absence of a signal generated from the binding or interaction of the compound with the polypeptide or polynucleotide.

In accordance with yet another aspect of the invention, there are provided mecB agonists and antagonists, preferably bacteriostatic or bacteriocidal agonists and antagonists.

In a further aspect of the invention there are provided compositions comprising a mecB polynucleotide or a mecB polypeptide for administration to a cell or to a multicellular organism.

Various changes and modifications within the spirit and scope of the disclosed invention will become readily apparent to those skilled in the art from reading the following descriptions and from reading the other parts of the present disclosure.

DESCRIPTION OF THE INVENTION

The invention relates to novel mecB polypeptides and polynucleotides as described in greater detail below. In particular, the invention relates to polypeptides and polynucleotides of a novel mecB of *Staphylococcus aureus*, which is related by amino acid sequence homology to ClpC polypeptide. The invention relates especially to mecB having the nucleotide and amino acid sequences set out in Table 1 as SEQ ID NO: 1 and SEQ ID NO: 2 respectively.

TABLE 1 mecB Polynucleotide and Polypeptide Sequences (A) Sequences from *Staphylococcus aureus* mecB polynucleotide sequence [SEQ ID NO:1].

5'-

```
   1 ATGTTATTTG GTAGATTAAC TGAACGTGCA CAGCGCGTAT TAGCACATGC
  51 ACAAGAAGAA GCAATTCGTT TAAATCATTC TAATATAGGA ACAGAACACC
 101 TATTATTGGG GTTAATGAAA GAACCTGAAG GAATTGCTGC AAAAGTATTA
 151 GAAAGTTTTA ATATCACTGA AGATAAAGTA ATTGAAGAAG TTGAAAAATT
 201 AATCGGACAT GGTCAAGATC ATGTTGGTAC ATTGCATTAT ACACCTAGAG
 251 CTAAAAAAGT CATTGAATTA TCGATGGATG AAGCTAGAAA ATTACATCAC
 301 AATTTTGTTG GAACGGTTCA TCTTTTATTA GGCTTGATTC GTGAAAATGA
 351 AGGTGTTGCA GCAAGAGTTT TTGCAAATCT AGATTTAAAT ATTACTAAAG
 401 CGCGTGCACG GGTTGTGAAA GCTTTAGGAA ACCCTGAAAT GAGTAATAAA
 451 AATGCACAAG CTAGTAAGTC AAATAATACT CCAACTTTAG ATAGTTTAGC
 501 TCGTGACTTA ACAGTCATTG CCAAAGACGG TACATTAGAT CCTGTTATAG
 551 GACGTGATAA AGAAATTACA CGTGTAATTG AAGTATTAAG TAGACGTACG
 601 AAAAACAATC CTGTACTTAT TGGAGAGCCA GGTGTTGGTA AAACTGCTAT
 651 TGCTGAAGGT TTAGCGCAAG CCATAGTGAA TAATGAGGTA CCAGAGACAT
 701 TAAAAGATAA GCGTGTTATG TCTTTAGATA TGGGAACAGT AGTTGCAGGT
 751 ACTAAATATC GTGGTGAATT TGAAGAGCGT CTGAAAAAGG TTATGGAAGA
 801 AATCCAACAA GCAGGTAATG TCATCCTATT TATTGATGAG TTGCATACTT
 851 TAGTTGGTGC TGGTGGTGCT GAAGGTGCTA TCGATGCTTC GAATATTTTG
 901 AAACCGGCAT TAGCACGTGG TGAATTACAA TGTATTGGTG CTACTACATT
 951 AGATGAATAT CGCAAAAATA TTGAAAAAGA CGCGGCTTTA GAACGTCGTT
1001 TCCAACCTGT ACAAGTTGAT GAACCTTCAG TAGTAGATAC AGTTGCTATT
1051 TTAAAAGGAT TAAGAGATCG TTACGAAGCA CACCATCGTA TTAATATTTC
1101 AGACGAAGCT ATTGAAGCAG CTGTTAAATT AAGTAACAGA TACGTTTCAG
1151 ATCGTTTCTT ACCAGATAAA GCAATTGATT TAATTGATGA AGCAAGTTCT
1201 AAAGTAAGAC TTAAGAGTCA TACGACACCT AATAATTTAA AAGAAATTGA
1251 ACAAGAAATT GAAAAAGTTA AAAATGAAAA AGATGCCGCA GTACATGCTC
1301 AAGAGTTTGA AAATGCTGCT AACCTGCGTG ATAAACAAAC AAAACTTGAA
1351 AAGCAATATG AAGAAGCTAA AAATGAATGG AAGAATGCAC AAAATGGCAT
```

TABLE 1-continued mecB Polynucleotide and Polypeptide Sequences

1401 GTCAACTTCA TTGTCAGAAG AAGATATTGC TGAAGTTATT GCAGGATGGA

1451 CAGGTATCCC ATTAACTAAA ATCAATGAAA CAGAATCTGA AAAACTTCTT

1501 AGTCTAGAAG ATACATTACA TGAGAGAGTT ATTGGGCAAA AAGATGCTGT

1551 TAATTCAATC AGTAAAGCGG TTAGACGTGC CCGTGCAGGG TTAAAAGATC

1601 CTAAACGACC AATTGGTAGC TTTATCTTCC TTGGACCAAC TGGTGTTGGT

1651 AAAACTGAAT TAGCTAGAGC TTTAGCTGAA TCAATGTTTG GCGATGATGA

1701 TGCGATGATC CGTGTAGACA TGAGTGAATT TATGGAAAAA CACGCAGTGA

1751 GCCGATTAGT TGGTGCTCCT CCAGGATATG TTGGTCATGA TGATGGTGGA

1801 CAATTAACTG AAAAAGTTAG ACGTAAACCA TATTCTGTAA TTTTATTTGA

1851 TGAAATTGAA AAAGCTCATC CAGATGTATT TAATATTCTA TTACAAGTTT

1901 TAGATGATGG ACATTTGACA GATACAAAAG GACGTACAGT TGATTTCAGA

1951 AATACAATTA TCATAATGAC ATCAAACGTT GGGGCACAAG AATTACAAGA

2001 TCAACGATTT GCTGGATTCG GTGGTTCAAG TGATGGACAA GATTATGAAA

2051 CAATTCGAAA AACGATGTTA AAAGAATTAA AAAATTCATT CCGTCCAGAA

2101 TTTTTAAACC GTGTAGATGA TATCATTGTA TTCCATAAAC TAACAAAAGA

2151 AGAATTAAAA GAAATTGTAA CAATGATGGT TAATAAAATTA ACAAATCGAT

2201 TATCTGAACA AACATAAAT ATTATTGTTA CTGATAAAGC GAAAGACAAA

2251 ATCGCAGAAG AAGGATATGA TCCAGAATAT GGTGCAAGAC CATTAATTAG

2301 AGCGATACAA AAAACTATCG AAGATAATTT AAGTGAATTA ATATTAGATG

2351 GTAATCAAAT TGAAGGTAAG AAAGTTACAG TAGATCATGA TGGTAAAGAG

2401 TTTAAATATG ACATTGCTGA ACAAACTTCA GAAACTAAAA CACCATCGCA

2451 AGCATAATTA TAAAACAGTC CAAAACAAAT TAAAGTTTTG GGCTGTTTTT

2501 TTAGTAGCAT TGAACTATAG AAATTCGTGA AAGTATCCAT CAACGAAACA

2551 ATCTAATAAA ACAATCATCA AAGGATAGTT AAGAATTATA TGTAACAAG-3'

(B) *Staphylococcus aureus* mecB polypeptide sequence deduced from the polynucleotide sequence in this table [SEQ ID NO:2].

NH₂-

1 MLFGRLTERA QRVLAHAQEE AIRLNHSNIG TEHLLLGLMK EPEGIAAKVL

51 ESFNITEDKV IEEVEKLJGH GQDHVGTLHY TPRAKKVTEL SMDEARKLHH

101 NFVGTVHLLL GLIRENEGVA ARVFANLDLN JTKARARVVK ALGNPEMSNK

151 NAQASKSNNT PTLDSLARDL TVIAKDGTLD PVIGRDKEIT RVIEVLSRRT

201 KNNPVLIGEP GVGKTAIAEG LAQAIVNNEV PETLKDKRVM SLDMGTVVAG

251 TKYRGEFEER LKKVMEEIQQ AGNVILFIDE LHTLVGAGGA EGAIDASNIL

301 KPALARGELQ CIGATTLDEY RKNIEKDAAL ERRFQPVQVD EPSVVDTVAI

351 LKGLRDRYEA HHRJNISDEA IEAAVKLSNR YVSDRFLPDK AIDLIDEASS

401 KVRLKSHTTP NNLKEIEQEI EKVKNEKDAA VHAQEFENAA NLRDKQTKLE

451 KQYEEAKNEW KNAQNGMSTS LSEEDIAEVI AGWTGIPLTK INETESEKLL

501 SLEDTLHERV IGQKDAVNSI SKAVRRARAG LKDPKRPIGS FIFLGPTGVG

TABLE 1-continued mecB Polynucleotide and Polypeptide Sequences

551 KTELARALAE SMFGDDDAMI RVDMSEFMEK HAVSRLVGAP PGYVGHDDGG

601 QLTEKVRRKP YSVILFDEIE KAHPDVFNIL LQVLDDGHLT DTKGRTVDFR

651 NTIIIMTSNV GAQELQDQRF AGFGGSSDGQ DYETIRKTML KELKNSFRPE

701 FLNRVDDIIV FHKLTKEELK EIVTMMVNKL TNRLSEQNIN IIVTDKAKDK

751 IAEEGYDPEY GARPLIRAIQ KTIEDNLSEL ILDGNQIEGK KVTVDHDGKE

801 FKYDIAEQTS ETKTPSQA*L *NSPKQIKVL GCFFSSIEL* KFVKVSINET

851 I**NNHQRIV KNYM*Q

-COOH (C) Polynucleotide sequences comprising *Staphylococcus aureus* mecB ORF sequence [SEQ ID NO:3].

5'-

```
   1 ATGAGTAATA AAAATGCACA AGCTAGTAAG TCAAATAATA CTCCAACTTT
  51 AGATAGTTTA GCTCGTGACT TAACAGTCAT TGCCAAAGAC GGTACATTAG
 101 ATCCTGTTAT AGGACGTGAT AAAGAAATTA CACGTGTAAT TGAAGTATTA
 151 AGTAGACGTA CGAAAAACAA TCCTGTACTT ATTGGAGAGC CAGGTGTTGG
 201 TAAAACTGCT ATTGCTGAAG GTTTAGCGCA AGCCATAGTG AATAATGAGG
 251 TACCAGAGAC ATTAAAAGAT AAGCGTGTTA TGTCTTTAGA TATGGGAACA
 301 GTAGTTGCAG GTACTAAATA TCGTGGTGAA TTTGAAGAGC GTCTGAAAAA
 351 GGTTATGGAA GAAATCCAAC AAGCAGGTAA TGTCATCCTA TTTATTGATG
 401 AGTTGCATAC TTTAGTTGGT GCTGGTGGTG CTGAAGGTGC TATCGATGCT
 451 TCGAATATTT TGAAACCGGC ATTAGCACGT GGTGAATTAC AATGTATTGG
 501 TGCTACTACA TTAGATGAAT ATCGCAAAAA TATTGAAAAA GACGCGGCTT
 551 TAGAACGTCG TTTCCAACCT GTACAAGTTG ATGAACTTTC AGTAGTAGAT
 601 ACAGTTGCTA TTTTAAAAGG ATTAAGAGAT CGTTACGAAG CACACCATCG
 651 TATTAATATT TCAGACGAAG CTATTGAAGC AGCTGTTAAA TTAAGTAACA
 701 GATACGTTTC AGATCGTTTC TTACCAGATA AAGCAATTGA TTTAATTGAT
 751 GAAGCAAGTT CTAAAGTAAG ACTTAAGAGT CATACGACAC TAATAATTTT
 801 AAAAGAAATT GAACAAGAAA TTGAAAAAGT TAAAAATGAA AAAGATGCCG
 851 CAGTACATGC TCAAGAGTTT GAAAATGCTG CTAACCTGCG TGATAAACAA
 901 ACAAAACTTG AAAAGCAATA TGAAGAAGCT AAAAATGAAT GGAAGAATGC
 951 ACAAAATGGC ATGTCAACTT CATTGTCAGA GAAGATATT GCTGAAGTTA
1001 TTGCAGGATG GACAGGTATC CCATTAACTA AAATCAATGA AACAGAATCT
1051 GAAAAACTTC TTAGTCTAGA AGATACATTA CATGAGAGAG TTATTGGGCA
1101 AAAAGATGCT GTTAATTCAA TCAGTAAAGC GGTTAGACGT GCCCGTGCAG
1151 GGTTAAAAGA TCCTAAACGA CCAATTGGTA GCTTTATCTT CCTTGGACCA
1201 ACTGGTGTTG CTAAAACTGA ATTAGCTAGA GCTTTAGCTG AATCAATGTT
1251 TGGCGATGAT GATGCGATGA TCCGTGTAGA CATGAGTGAA TTTATGGAAA
1301 AACACGCAGT GAGCCGATTA GTTGGTGCTC CTCCAGGATA TGTTGGTCAT
1351 GATGATGGTG GACAATTAAC TGAAAAAGTT AGACGTAAAC CATATTCTGT
```

TABLE 1-continued mecB Polynucleotide and Polypeptide Sequences

```
1401 AATTTTATTT GATCAAATTG AAAAAGCTCA TCCAGATGTA TTTAATATTC

1451 TATTACAAGT TTTAGATGAT GGACATTTGA CAGATACAAA AGGACGTACA

1501 GTTGATTTCA GAAATACAAT TATCATAATG ACATCAAACG TTGGGGCACA

1551 AGAATTACAA GATCAACGAT TTGCTGGATT CGGTGGTTCA AGTGATGGAC

1601 AAGATTATGA AACAATTCGA AAAACGATGT TAAAAGAATT AAAAAATTCA

1651 TTCCGTCCAG AATTTTTAAA CCGTGTAGAT GATATCATTG TATTCCATAA

1701 ACTAACAAAA GAAGAATTAA AAGAAATTGT AACAATGATG GTTAATAAAT

1751 TAACAAATCG ATTATCTGAA CAAAACATAA ATATTATTGT TACTGATAAA

1801 GCGAAAGACA AAATCGCAGA AGAAGGATAT GATCCAGAAT ATGGTGCAAG

1851 ACCATTAATT AGAGCGATAC AAAAAACTAT CGAAGATAAT TTAAGTGAAT

1901 TAATATTAGA TGGTAATCAA ATTGAAGGTA AGAAAGTTAC AGTAGATCAT

1951 GATGGTAAAG AGTTTAAATA TGACATTGCT GAACAAACTT CAGAAACTAA

2001 AACACCATCG CAACCATAA

-3'
```

(D) *Staphylococcus aureus* mecB polypeptide sequence deduced from the polynucleotide ORF sequence in this table [SEQ ID NO:4].

NH$_2$-

```
  1 MSNKNAQASK SNNTPTLDSL ARDLTVIAKD GTLDPVIGRD KEITRVIEVL

51 SRRTKNNPVL IGEPGVGKTA IAEGLAQAJV NNEVPETLKD KRVMSLDMGT

101 VVAGTKYRGE FEERLKKVME EIQQAGNVIL FIDELHTLVG AGGAEGAIDA

151 SNILKPALAR GELQCIGATT LDEYRKNIEK DAALERRFQP VQVDEPSVVD

201 TVAILKGLRD RYEAHHRINI SDEAIEAAVK LSNRYVSDRF LPDKAIDLID

251 EASSKVRLKS HTTPNNLKEI EQEIEKVKNE KDAAVHAQEF ENAANLRDKQ

301 TKLEKQYEEA KNEWKNAQNG MSTSLSEEDI AEVIAGWTGI PLTKINETES

351 EKLLSLEDTL HERVIGQKDA VNSISKAVRR ARAGLKDPKR PIGSFIFLGP

401 TCVGKTELAR ALAESMFGDD DAMIRVDMSE FMEKHAVSRL VGAPPGYVGH

451 DDGGQLTEKV RRKPYSVILF DEIEKAHPDV FNILLQVLDD GHLTDTKGRT

501 VDFRNTIIIM TSNVGAQELQ DQRFAGFGGS SDGQDYETIR KTMLKELKNS

551 FRPEFLNRVD DIIVFHKLTK EELKEIVTMM VNKLTNRLSE QNINIIVTDK

601 AKDKIAEEGY DPEYGARPLI PAIQKTIEDN LSELJLDGNQ IEGKKVTVDH

651 DGKEFKYDIA EQTSETKTPS QA
```

-COOH

Deposited Materials

A deposit containing a *Staphylococcus aureus* WCUH 29 strain has been deposited with the National Collections of Industrial and Marine Bacteria Ltd. (herein "NCIMB"), 23 St. Machar Drive, Aberdeen AB2 1RY, Scotland on Sep. 11, 1995 and assigned NCIMB Deposit No. 40771, and referred to as *Staphylococcus aureus* WCUH29 on deposit. The *Staphylococcus aureus* strain deposit is referred to herein as "the deposited strain" or as "the DNA of the deposited strain."

The deposited strain contains the full length mecB gene. The sequence of the polynucleotides contained in the deposited strain, as well as the amino acid sequence of the polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

A license may be required to make, use or sell the deposited strain, and compounds derived therefrom, and no such license is hereby granted.

One aspect of the invention there is provided an isolated nucleic acid molecule encoding a mature polypeptide expressible by the Staphylococcus aureus WCUH 29 strain contained in the deposited strain. Further provided by the invention are mecB nucleotide sequences of the DNA in the deposited strain and amino acid sequences encoded thereby. Also provided by the invention are mecB polypeptide sequences isolated from the deposited strain and amino acid sequences derived therefrom.

Polypeptides

The polypeptides of the invention include a polypeptide of Table 1 [SEQ ID NO:2 or 4] (in particular the mature polypeptide) as well as polypeptides and fragments, particularly those which have the biological activity of mecB, and also those which have at least 70% identity to a polypeptide of Table 1 [SEQ ID NO:1 or 3] or the relevant portion, preferably at least 80% identity to a polypeptide of Table 1 [SEQ ID NO:2 or 4] and more preferably at least 90% similarity (more preferably at least 90% identity) to a polypeptide of Table 1 [SEQ ID NO:2 or 4] and still more preferably at least 95% similarity (still more preferably at least 95% identity) to a polypeptide of Table 1 [SEQ ID NO:2 or 4] and also include portions of such polypeptides with such portion of the polypeptide generally containing at least 30 amino acids and more preferably at least 50 amino acids.

The invention also includes polypeptides of the formula:

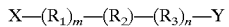

$$X—(R_1)_m—(R_2)—(R_3)_n—Y$$

wherein, at the amino terminus, X is hydrogen, and at the carboxyl terminus, Y is hydrogen or a metal, $R_1$ and $R_3$ are any amino acid residue, m is an integer between 1 and 1000 or zero, n is an integer between 1 and 1000 or zero, and $R_2$ is an amino acid sequence of the invention, particularly an amino acid sequence selected from Table 1. In the formula above $R_2$ is oriented so that its amino terminal residue is at the left, bound to $R_1$, and its carboxy terminal residue is at the right, bound to $R_3$. Any stretch of amino acid residues denoted by either R group, where m and/or n is greater than 1, may be either a heteropolymer or a homopolymer, preferably a heteropolymer. A fragment is a variant polypeptide having an amino acid sequence that entirely is the same as part but not all of the amino acid sequence of the aforementioned polypeptides. As with mecB polypeptides fragments may be "free-standing," or comprised within a larger polypeptide of which they form a part or region, most preferably as a single continuous region, a single larger polypeptide.

Preferred fragments include, for example, truncation polypeptides having a portion of an amino acid sequence of Table 1 [SEQ ID NO:2 or 4], or of variants thereof, such as a continuous series of residues that includes the amino terminus, or a continuous series of residues that includes the carboxyl terminus. Degradation forms of the polypeptides of the invention in a host cell, particularly a Staphylococcus aureus, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of mecB, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of Staphylococcus aureus or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the fill-length polypeptides of the invention.

In addition to the standard single and triple letter representations for amino acids, the term "X" or "Xaa" may also be used in describing certain polypeptides of the invention. "X" and "Xaa" mean that any of the twenty naturally occuring amino acids may appear at such a designated position in the polypeptide sequence.

Polynucleotides

Another aspect of the invention relates to isolated polynucleotides, including the fill length gene, that encode the mecB polypeptide having a deduced amino acid sequence of Table 1 [SEQ ID NO:2 or 4] and polynucleotides closely related thereto and variants thereof.

Using the information provided herein, such as a polynucleotide sequence set out in Table 1 [SEQ ID NO:1 or 3], a polynucleotide of the invention encoding mecB polypeptide may be obtained using standard cloning and screening methods, such as those for cloning and sequencing chromosomal DNA fragments from bacteria using Staphylococcus aureus WCUH 29 cells as starting material, followed by obtaining a full length clone. For example, to obtain a polynucleotide sequence of the invention, such as a sequence given in Table 1 [SEQ ID NO:1 or 3], typically a library of clones of chromosomal DNA of Staphylococcus aureus WCUH 29 in E.coli or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., MOLECULAR CLONING, A LABORATORY MANUAL, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Illustrative of the invention, the polynucleotide set out in Table 1 [SEQ ID NO:1 or 3] was discovered in a DNA library derived from Staphylococcus aureus WCUH 29.

The DNA sequence set out in Table 1 [SEQ ID NO: 1 or 3] contains an open reading frame encoding a protein having about the number of amino acid residues set forth in Table 1 [SEQ ID NO:2 or 4] with a deduced molecular weight that can be calculated using amino acid residue molecular weight values well known in the art. The polynucleotide of SEQ ID NO: 1, between nucleotide number 1 and the stop codon which begins at nucleotide number 2455 of SEQ ID NO: 1, encodes the polypeptide of SEQ ID NO:2.

MecB of the invention is structurally related to other proteins of the ClpC ATPase family.

The invention provides a polynucleotide sequence identical over its entire length to a coding sequence in Table 1 [SEQ ID NO: 1 or 3]. Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro- protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., Proc. Natl. Acad. Sci., USA 86: 821–824 (1989), or an HA tag (Wilson et al., Cell 37: 767 (1984). Polynucleotides of the invention also include, but are not limited to, polynucleotides comprising a structural gene and its naturally associated sequences that control gene expression.

A preferred embodiment of the invention is a polynucleotide of comprising nucleotide 1 to the nucleotide immediately upstream of or including nucleotide 2455 set forth in SEQ ID NO: 1 of Table 1, both of which encode the mecB polypeptide.

The invention also includes polynucleotides of the formula:

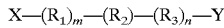

wherein, at the 5' end of the molecule, X is hydrogen or together with Y defines a covalent bond, and at the 3' end of the molecule, Y is hydrogen or a metal or together with X defines the covalent bond, each occurance of $R_1$ and $R_3$ is independently any nucleic acid residue, m is an integer between 1 and 3000 or zero, n is an integer between 1 and 3000 or zero, and $R_2$ is a nucleic acid sequence of the invention, particularly a nucleic acid sequence selected from Table 1. In the polynucleotide formula above $R_2$ is oriented so that its 5' end residue is at the left, bound to $R_1$ and its 3' end residue is at the right, bound to $R_3$. Any stretch of nucleic acid residues denoted by either R group, where m and/or n is greater than 1, may be either a heteropolymer or a homopolymer, preferably a heteropolymer. Where, in a preferred embodiment, X and Y together define a covalent bond, the polynucleotide of the above formula is a closed, circular polynucleotide, which can be a double-stranded polynucleotide wherein the formula shows a first strand to which the second strand is complementary. In another preferred embodiment m and/or n is an integer between 1 and 1000.

It is most preferred that the polynucleotides of the inventions are derived from Staphylococcus aureus, however, they may preferably be obtained from organisms of the same taxonomic genus. They may also be obtained, for example, from organisms of the same taxonomic family or order.

The term "polynucleotide encoding a polypeptide" as used herein encompasses polynucleotides that include a sequence encoding a polypeptide of the invention, particularly a bacterial polypeptide and more particularly a polypeptide of the Staphylococcus aureus mecB having an amino acid sequence set out in Table 1 [SEQ ID NO:2 or 4]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having a deduced amino acid sequence of Table 1 [SEQ ID NO:2 or 4]. Variants that are fragments of the polynucleotides of the invention may be used to synthesize full-length polynucleotides of the invention.

Further particularly preferred embodiments are polynucleotides encoding mecB variants, that have the amino acid sequence of mecB polypeptide of Table 1 [SEQ ID NO:2 or 4] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of mecB.

Further preferred embodiments of the invention are polynucleotides that are at least 70% identical over their entire length to a polynucleotide encoding mecB polypeptide having an amino acid sequence set out in Table 1 [SEQ ID NO:2 or 4], and polynucleotides that are complementary to such polynucleotides. Alternatively, most highly preferred are polynucleotides that comprise a region that is at least 80% identical over its entire length to a polynucleotide encoding mecB polypeptide and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides that encode polypeptides that retain substantially the same biological function or activity as the mature polypeptide encoded by a DNA of Table 1 [SEQ ID NO: 1 or 3].

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 micrograms/ml denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in SEQ ID NO:1 under stringent hybridization conditions with a probe having the sequence of said polynucleotide sequence set forth in SEQ ID NO:1 or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding mecB and to isolate cDNA and genomic clones of other genes that have a high sequence similarity to the mecB gene. Such probes generally will comprise at least 15 bases. Preferably, such probes will have at least 30 bases and may have at least 50 bases. Particularly preferred probes will have at least 30 bases and will have 50 bases or less.

For example, the coding region of the mecB gene may be isolated by screening using a DNA sequence provided in Table 1 [SEQ ID NO: 1 or 3] to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed, for example, as research reagents and materials for discovery of treatments of and diagnostics for disease, particularly human disease, as further discussed herein relating to polynucleotide assays.

Polynucleotides of the invention that are oligonucleotides derived from the sequences of Table 1 [SEQ ID NOS: 1 or 2 or 3 or 4] may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleic acid bases, the term "N" may also be used in describing certain polynucleotides of the invention. "N" means that any of the four DNA or RNA bases may appear at such a designated position in the DNA or RNA sequence, except it is preferred that N is not a base that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., *BASIC METHODS IN MOLECULAR BIOLOGY*, (1986) and Sambrook et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, enterococci *E. coli*, streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the mecB polynucleotides of the invention for use as diagnostic reagents. Detection of mecB in a eukaryote, particularly a mammal, and especially a human, will provide a diagnostic method for diagnosis of a disease. Eukaryotes (herein also "individual(s)"), particularly mammals, and especially humans, particularly those infected or suspected to be infected with an organism comprising the mecB gene may be detected at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA, cDNA and genomic DNA may also be used in the same ways. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled mecB polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., *Science,* 230: 1242 (1985). Sequence changes at specific locations also may be revealed by nuclease protection assays, such as RNase and S1 protection or a chemical cleavage method. See, e.g., Cotton et al., *Proc. Natl. Acad. Sci., USA,* 85: 4397–4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA, cDNA or genomic DNA may also be used for the same purpose, PCR or RT-PCR. As an example, PCR primers complementary to a nucleic acid encoding mecB can be used to identify and analyze mutations. Examples of representative primers are shown below in Table 2.

TABLE 2

Primers for amplification of mecB polynucleotides

| SEQ ID NO | PRIMER SEQUENCE |
|---|---|
| 5 | 5'-atagcaactgtatctactactgaagg-3' |
| 6 | 5'-aattgaagtattaagtagacgtacg-3' |

The invention also includes primers of the formula:

$$X—(R_1)_m—(R_2)—(R_3)_n—Y$$

wherein, at the 5' end of the molecule, X is hydrogen, and at the 3' end of the molecule, Y is hydrogen or a metal, $R_1$ and $R_3$ is any nucleic acid residue, m is an integer between 1 and 20 or zero, n is an integer between 1 and 20 or zero, and $R_2$ is a primer sequence of the invention, particularly a primer sequence selected from Table 2. In the polynucleotide formula above $R_2$ is oriented so that its 5' end residue is at the left, bound to $R_1$, and its 3' end residue is at the right, bound to $R_3$. Any stretch of nucleic acid residues denoted by either R group, where m and/or n is greater than 1, may be either a heteropolymer or a homopolymer, preferably a heteropolymer being complementary to a region of a polynucleotide of Table 1. In a preferred embodiment m and/or n is an integer between 1 and 10.

The invention further provides these primers with 1, 2, 3 or 4 nucleotides removed from the 5' and/or the 3' end. These primers may be used for, among other things, amplifying mecB DNA isolated from a sample derived from an individual. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by *Staphylococcus aureus,* comprising determining from a sample derived from an individual a increased level of expression of polynucleotide having a sequence of Table 1 [SEQ ID NO: 1 or 3]. Increased or decreased expression of mecB polynucleotide can be measured using any on of the methods well known in the art for the quantation of polynucleotides, such as, for example, amplification, PCR, RT-PCR, RNase protection, Northern blotting and other hybridization methods.

In addition, a diagnostic assay in accordance with the invention for detecting over-expression of mecB protein compared to normal control tissue samples may be used to detect the presence of an infection, for example. Assay techniques that can be used to determine levels of a mecB protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., Nature 256: 495–497 (1975); Kozbor et al., Immunology Today 4: 72 (1983); Cole et al., pg. 77–96 in MONOCLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing anti-mecB or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against mecB-polypeptide may be employed to treat infections, particularly bacterial infections.

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), Nature 321, 522–525 or Tempest et al., (1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem. 1989: 264,16985), coprecipitation of DNA with calcium phosphate (3envenisty & Reshef, PNAS USA, 1986:83,9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS USA 1984:81,5849).

Antagonists and Agonists—Assays and Molecules

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., Current Protocols in Immunology 1(2): Chapter 5 (1991).

The invention also provides a method of screening compounds to identify those which enhance (agonist) or block (antagonist) the action of mecB polypeptides or polynucleotides, particularly those compounds that are bacteriostatic and/or bacteriocidal. The method of screening may involve high-throughput techniques. For example, to screen for agonists or antagoists, a synthetic reaction mix, a cellular compartment, such as a membrane, cell envelope or cell wall, or a preparation of any thereof, comprising mecB polypeptide and a labeled substrate or ligand of such polypeptide is incubated in the absence or the presence of a candidate molecule that may be a mecB agonist or antagonist. The ability of the candidate molecule to agonize or antagonize the mecB polypeptide is reflected in decreased binding of the labeled ligand or decreased production of product from such substrate. Molecules that bind gratuitously, i.e., without inducing the effects of mecB polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to changes in mecB polynucleotide or polypeptide activity, and binding assays known in the art.

Another example of an assay for mecB antagonists is a competitive assay that combines mecB and a potential antagonist with mecB-binding molecules, recombinant mecB binding molecules, natural substrates or ligands, or substrate or ligand mimetics, under appropriate conditions for a competitive inhibition assay. MecB can be labeled, such as by radioactivity or a colorimetric compound, such that the number of mecB molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing mecB-induced activities, thereby preventing the action of mecB by excluding mecB from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLE-OTIDES AS ANTISENSE INHIBITORS OF GENE EXPRESSION,* CRC Press, Boca Raton, Fla. (1988), for a description of these molecules). Preferred potential antagonists include compounds related to and variants of mecB.

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgamo or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block mecB protein-mediated mammalian cell invasion by, for example, initiating phosphorylation of mammalian tyrosine kinases (Rosenshine et al., *Infect. Immun.* 60:2211 (1992); to block bacterial adhesion between mammalian extracellular matrix proteins and bacterial mecB proteins that mediate tissue damage and; to block the normal progression of pathogenesis in infections initiated other than by the implantation of in-dwelling devices or by other surgical techniques.

The antagonists and agonists of the invention may be employed, for instance, to inhibit and treat diseases.

*Helicobacter pylori* (herein *H. pylori*) bacteria infect the stomachs of over one-third of the world's population causing stomach cancer, ulcers, and gastritis (International Agency for Research on Cancer (1994) Schistosomes, Liver Flukes and Helicobacter Pylori (International Agency for Research on Cancer, Lyon, France; http://www.uicc.ch/ecp/ecp2904.htm). Moreover, the international Agency for Research on Cancer recently recognized a cause-and-effect relationship between *H. pylori* and gastric adenocarcinoma, classifying the bacterium as a Group I (definite) carcinogen. Preferred antimicrobial compounds of the invention (agonists and antagonists of mecB) found using screens provided by the invention, particularly broad-spectrum antibiotics, should be useful in the treatment of *H. pylori* infection. Such treatment should decrease the advent of *H. pylori*-induced cancers, such as gastrointestinal carcinoma.

Such treatment should also cure gastric ulcers and gastritis.

Vaccines

Another aspect of the invention relates to a method for inducing an immunological response in an individual, particularly a mammal which comprises inoculating the individual with mecB, or a fragment or variant thereof, adequate to produce antibody and/or T cell immune response to protect said individual from infection, particularly bacterial infection and most particularly *Staphylococcus aureus* infection. Also provided are methods whereby such immunological response slows bacterial replication. Yet another aspect of the invention relates to a method of inducing immunological response in an individual which comprises delivering to such individual a nucleic acid vector to direct expression of mecB, or a fragment or a variant thereof, for expressing mecB, or a fragment or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to a mecB or protein coded therefrom, wherein the composition comprises a recombinant mecB or protein coded therefrom comprising DNA which codes for and expresses an antigen of said mecB or protein coded therefrom. The immunological response may be used therapeutically or prophylactically and may take the form of antibody immunity or cellular immunity such as that arising from CTL or CD4+ T cells.

A mecB polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae,* Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Staphylococcus aureus* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain mecB protein, it is to be understood that this covers fragments of the naturally occurring protein and similar proteins with additions, deletions or substitutions which do not substantially affect the immunogenic properties of the recombinant protein.

Compositions, Kits and Administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *Staphylococcus aureus* wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 $\mu$g/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

GLOSSARY

The following definitions are provided to facilitate understanding of certain terms used frequently herein.

"Disease(s)" means and disease caused by or related to infection by a bacteria, including disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellultis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis).

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following:

1) Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:

1) Algorithm: Needleman and Wunsch, J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO: 1, wherein said polynucleotide sequence may be identical to the reference sequence of SEQ ID NO: 1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO: 1 by the integer defining the percent identity divided by 100 and then subtracting that product from said total number of nucleotides in SEQ ID NO: 1, or:

$$n_n \leq x_n - (x_n \cdot y),$$

wherein $n_n$ in is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or $_3$' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of amino acids in SEQ ID NO:2 by the integer defining the percent identity divided by 100 and then subtracting that product from said total number of amino acids in SEQ ID NO:2, or:

$$n_n \leq x_n - (x_n \cdot y),$$

wherein $n_n$ is the number of amino acid alterations, $x_n$ is the total number of amino acids in SEQ ID NO:2, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO: 2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in 25 SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES,* 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS,* B. C. Johnson, Ed., Academic Press, New York (1983); Seifter et al., *Meth. Enzymol.* 182:626–646 (1990) and Rattan et al., *Protein Synthesis: Posttranslational Modifications and Aging,* Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

EXAMPLES

The examples below are carried out using standard techniques, which are well known and routine to those of skill in the art, except where otherwise described in detail. The examples are illustrative, but do not limit the invention.

Example 1

Strain Selection, Library Production and Sequencing

The polynucleotide having a DNA sequence given in Table 1 [SEQ ID NO: 1 or 3] was obtained from a library of clones of chromosomal DNA of *Staphylococcus aureus* in *E. coli.* The sequencing data from two or more clones containing overlapping *Staphylococcus aureus* DNAs was used to construct the contiguous DNA sequence in SEQ ID NO: 1. Libraries may be prepared by routine methods, for example: Methods 1 and 2 below.

Total cellular DNA is isolated from *Staphylococcus aureus* WCUH 29 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRi, the library packaged by standard procedures and *E. coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

What is claimed is:

1. An isolated polynucleotide segment comprising a first polynucleotide sequence or the full complement of the entire length of the first polynucleotide sequence, wherein the first polynucleotide sequence encodes a polypeptide comprising the amino acid sequence set forth in SEQ ID NO:2.

2. The isolated polynucleotide segment of claim 1, wherein the isolated polynucleotide segment comprises the first polynucleotide sequence.

3. A vector comprising the isolated polynucleotide segment of claim 2.

4. An isolated host cell comprising the vector of claim 3.

5. A process for producing a polypeptide comprising the step of culturing the host cell of claim 4 under conditions sufficient for the production of the polypeptide, wherein the polypeptide is encoded by the first polynucleotide sequence.

6. The isolated polynucleotide segment of claim 1, wherein the isolated polynucleotide segment comprises the full complement of the entire length of the first polynucleotide sequence.

7. A vector comprising the isolated polynucleotide segment of claim 6.

8. An isolated host cell comprising the vector of claim 7.

9. A polynucleotide which encodes a fusion polypeptide and which includes the isolated polynucleotide segment according to claim 2.

10. An isolated polynucleotide segment comprising a first polynucleotide sequence or the full complement of the entire length of the first polynucleotide sequence, wherein the first polynucleotide sequence is identical to SEQ ID NO: 1, except that, over the entire length corresponding to SEQ ID NO:1, $n_n$ nucleotides are substituted, inserted or deleted, wherein $n_n$ satisfies the following expression $$n_n \leq x_n - (x_n \cdot y)$$

wherein $x_n$ is the total number of nucleotides in SEQ ID NO: 1, y is at least 0.998, and wherein any non-integer product of $x_n$ and y is rounded down to the nearest integer before subtracting the product from $x_n$.

11. A vector comprising the isolated polynucleotide segment of claim 10.

12. An isolated host cell comprising the vector of claim 11.

13. An isolated polynucleotide segment comprising a first polynucleotide sequence or the full complement of the entire length of the first polynucleotide sequence, wherein the first polynucleotide sequence comprises SEQ ID NO: 1.

14. The isolated polynucleotide segment of claim 13, wherein the isolated polynucleotide segment comprises the first polynucleotide sequence.

15. A vector comprising the isolated polynucleotide segment of claim 14.

16. An isolated host cell comprising the vector of claim 15.

17. A process for producing a polypeptide comprising the step of culturing the host cell of claim 16 under conditions sufficient for the production of the polypeptide, wherein the polypeptide is encoded by the first polynucleotide sequence.

18. The isolated polynucleotide segment of claim 13, wherein the isolated polynucleotide segment comprises the full complement of the entire length of the first polynucleotide sequence.

19. A vector comprising the isolated polynucleotide segment of claim 18.

20. An isolated host cell comprising the vector of claim 19.

21. A polynucleotide which encodes a fusion polypeptide and which includes the isolated polynucleotide segment according to claim 13.

22. An isolated polynucleotide segment comprising a first polynucleotide sequence or the full complement of the entire length of the first polynucleotide sequence, wherein the first polynucleotide sequence encodes a polypeptide consisting of the amino acid sequence set forth in SEQ ID NO:2.

23. The isolated polynucleotide segment of claim 22, wherein the isolated polynucleotide segment comprises the first polynucleotide sequence.

24. A vector comprising the isolated polynucleotide segment of claim 23.

25. An isolated host cell comprising the vector of claim 24.

26. A process for producing a polypeptide comprising the step of culturing the host cell of claim 25 under conditions sufficient for the production of the polypeptide, wherein the polypeptide is encoded by the first polynucleotide sequence.

27. The isolated polynucleotide segment of claim 22, wherein the isolated polynucleotide segment comprises the full complement of the entire length of the first polynucleotide sequence.

28. A vector comprising the isolated polynucleotide segment of claim 27.

29. An isolated host cell comprising the vector of claim 28.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2599 base pairs
      (B) TYPE: nucleic acid
      (C) STRANDEDNESS: double
      (D) TOPOLOGY: linear (xi) SEQUENCE DESCRIPTION: SEQ ID NO:1:

-continued

```
ATGTTATTTG GTAGATTAAC TGAACGTGCA CAGCGCGTAT AGCACATGC ACAAGAAGAA      60

GCAATTCGTT TAAATCATTC TAATATAGGA ACAGAACACC TATTATTGGG GTTAATGAAA    120

GAACCTGAAG GAATTGCTGC AAAAGTATTA GAAAGTTTTA ATATCACTGA AGATAAAGTA    180

ATTGAAGAAG TTGAAAAATT AATCGGACAT GGTCAAGATC ATGTTGGTAC ATTGCATTAT    240

ACACCTAGAG CTAAAAAAGT CATTGAATTA TCGATGGATG AAGCTAGAAA ATTACATCAC    300

AATTTTGTTG GAACGGTTCA TCTTTTATTA GGCTTGATTC GTGAAAATGA AGGTGTTGCA    360

GCAAGAGTTT TTGCAAATCT AGATTTAAAT ATTACTAAAG CGCGTGCACG GGTTGTGAAA    420

GCTTTAGGAA ACCCTGAAAT GAGTAATAAA AATGCACAAG CTAGTAAGTC AAATAATACT    480

CCAACTTTAG ATAGTTTAGC TCGTGACTTA ACAGTCATTG CCAAAGACGG TACATTAGAT    540

CCTGTTATAG GACGTGATAA AGAAATTACA CGTGTAATTG AAGTATTAAG TAGACGTACG    600

AAAAACAATC CTGTACTTAT TGGAGAGCCA GGTGTTGGTA AAACTGCTAT TGCTGAAGGT    660

TTAGCGCAAG CCATAGTGAA TAATGAGGTA CCAGAGACAT AAAAGATAA GCGTGTTATG     720

TCTTTAGATA TGGGAACAGT AGTTGCAGGT ACTAAATATC GTGGTGAATT TGAAGAGCGT    780

CTGAAAAAGG TTATGGAAGA AATCCAACAA GCAGGTAATG TCATCCTATT TATTGATGAG    840

TTGCATACTT TAGTTGGTGC TGGTGGTGCT GAAGGTGCTA TCGATGCTTC GAATATTTTG    900

AAACCGGCAT TAGCACGTGG TGAATTACAA TGTATTGGTG CTACTACATT AGATGAATAT    960

CGCAAAAATA TTGAAAAAGA CGCGGCTTTA GAACGTCGTT TCCAACCTGT ACAAGTTGAT   1020

GAACCTTCAG TAGTAGATAC AGTTGCTATT TTAAAAGGAT TAAGAGATCG TTACGAAGCA   1080

CACCATCGTA TTAATATTTC AGACGAAGCT ATTGAAGCAG CTGTTAAATT AAGTAACAGA   1140

TACGTTTCAG ATCGTTTCTT ACCAGATAAA GCAATTGATT TAATTGATGA AGCAAGTTCT   1200

AAAGTAAGAC TTAAGAGTCA TACGACACCT AATAATTTAA AAGAAATTGA ACAAGAAATT   1260

GAAAAAGTTA AAAATGAAAA AGATGCCGCA GTACATGCTC AAGAGTTTGA AAATGCTGCT   1320

AACCTGCGTG ATAAACAAAC AAAACTTGAA AAGCAATATG AAGAAGCTAA AAATGAATGG   1380

AAGAATGCAC AAAATGGCAT GTCAACTTCA TTGTCAGAAG AAGATATTGC TGAAGTTATT   1440

GCAGGATGGA CAGGTATCCC ATTAACTAAA ATCAATGAAA CAGAATCTGA AAAACTTCTT   1500

AGTCTAGAAG ATACATTACA TGAGAGAGTT ATTGGGCAAA AAGATGCTGT TAATTCAATC   1560

AGTAAAGCGG TTAGACGTGC CCGTGCAGGG TTAAAAGATC CTAAACGACC AATTGGTAGC   1620

TTTATCTTCC TTGGACCAAC TGGTGTTGGT AAAACTGAAT TAGCTAGAGC TTTAGCTGAA   1680

TCAATGTTTG GCGATGATGA TGCGATGATC CGTGTAGACA TGAGTGAATT TATGGAAAAA   1740

CACGCAGTGA GCCGATTAGT TGGTGCTCCT CCAGGATATG TTGGTCATGA TGATGGTGGA   1800

CAATTAACTG AAAAAGTTAG ACGTAAACCA TATTCTGTAA TTTTATTTGA TGAAATTGAA   1860

AAAGCTCATC CAGATGTATT TAATATTCTA TTACAAGTTT TAGATGATGG ACATTTGACA   1920

GATACAAAAG GACGTACAGT TGATTTCAGA AATACAATTA TCATAATGAC ATCAAACGTT   1980

GGGGCACAAG AATTACAAGA TCAACGATTT GCTGGATTCG GTGGTTCAAG TGATGGACAA   2040

GATTATGAAA CAATTCGAAA AACGATGTTA AAAGAATTAA AAAATTCATT CCGTCCAGAA   2100

TTTTTAAACC GTGTAGATGA TATCATTGTA TTCCATAAAC TAACAAAAGA AGAATTAAAA   2160

GAAATTGTAA CAATGATGGT TAATAAAATTA ACAAATCGAT TATCTGAACA AAACATAAAT   2220

ATTATTGTTA CTGATAAAGC GAAAGACAAA ATCGCAGAAG AAGGATATGA TCCAGAATAT   2280

GGTGCAAGAC CATTAATTAG AGCGATACAA AAAACTATCG AAGATAATTT AAGTGAATTA   2340
```

-continued

```
ATATTAGATG GTAATCAAAT TGAAGGTAAG AAAGTTACAG TAGATCATGA TGGTAAAGAG    2400

TTTAAATATG ACATTGCTGA ACAAACTTCA GAAACTAAAA CACCATCGCA AGCATAATTA    2460

TAAAACAGTC CAAAACAAAT TAAAGTTTTG GGCTGTTTTT TTAGTAGCAT TGAACTATAG    2520

AAATTCGTGA AGTATCCAT CAACGAAACA ATCTAATAAA ACAATCATCA AAGGATAGTT     2580

AAGAATTATA TGTAACAAG                                                 2599
```

(2) INFORMATION FOR SEQ ID NO:2:

(i) SEQUENCE CHARACTERISTICS:
        (A) LENGTH: 866 amino acids
        (B) TYPE: amino acid
        (C) STRANDEDNESS: single
        (D) TOPOLOGY: linear (xi) SEQUENCE DESCRIPTION: SEQ ID NO:2:

```
Met Leu Phe Gly Arg Leu Thr Glu Arg Ala Gln Arg Val Leu Ala His
 1               5                  10                  15

Ala Gln Glu Glu Ala Ile Arg Leu Asn His Ser Asn Ile Gly Thr Glu
            20                  25                  30

His Leu Leu Gly Leu Met Lys Glu Pro Glu Gly Ile Ala Ala Lys
        35                  40                  45

Val Leu Glu Ser Phe Asn Ile Thr Glu Asp Lys Val Ile Glu Val
    50                  55                  60

Glu Lys Leu Ile Gly His Gly Gln Asp His Val Gly Thr Leu His Tyr
65                  70                  75                  80

Thr Pro Arg Ala Lys Lys Val Ile Glu Leu Ser Met Asp Glu Ala Arg
                85                  90                  95

Lys Leu His His Asn Phe Val Gly Thr Val His Leu Leu Gly Leu
            100                 105                 110

Ile Arg Glu Asn Glu Gly Val Ala Ala Arg Val Phe Ala Asn Leu Asp
            115                 120                 125

Leu Asn Ile Thr Lys Ala Arg Ala Arg Val Val Lys Ala Leu Gly Asn
    130                 135                 140

Pro Glu Met Ser Asn Lys Asn Ala Gln Ala Ser Lys Ser Asn Asn Thr
145                 150                 155                 160

Pro Thr Leu Asp Ser Leu Ala Arg Asp Leu Thr Val Ile Ala Lys Asp
                165                 170                 175

Gly Thr Leu Asp Pro Val Ile Gly Arg Asp Lys Glu Ile Thr Arg Val
            180                 185                 190

Ile Glu Val Leu Ser Arg Arg Thr Lys Asn Asn Pro Val Leu Ile Gly
            195                 200                 205

Glu Pro Gly Val Gly Lys Thr Ala Ile Ala Glu Gly Leu Ala Gln Ala
    210                 215                 220

Ile Val Asn Asn Glu Val Pro Glu Thr Leu Lys Asp Lys Arg Val Met
225                 230                 235                 240

Ser Leu Asp Met Gly Thr Val Val Ala Gly Thr Lys Tyr Arg Gly Glu
                245                 250                 255

Phe Glu Glu Arg Leu Lys Lys Val Met Glu Glu Ile Gln Gln Ala Gly
            260                 265                 270

Asn Val Ile Leu Phe Ile Asp Glu Leu His Thr Leu Val Gly Ala Gly
            275                 280                 285

Gly Ala Glu Gly Ala Ile Asp Ala Ser Asn Ile Leu Lys Pro Ala Leu
    290                 295                 300

Ala Arg Gly Glu Leu Gln Cys Ile Gly Ala Thr Thr Leu Asp Glu Tyr
```

-continued

```
305                 310                 315                 320
Arg Lys Asn Ile Glu Lys Asp Ala Ala Leu Glu Arg Phe Gln Pro
                325                 330                 335
Val Gln Val Asp Glu Pro Ser Val Val Asp Thr Val Ala Ile Leu Lys
                340                 345                 350
Gly Leu Arg Asp Arg Tyr Glu Ala His His Arg Ile Asn Ile Ser Asp
                355                 360                 365
Glu Ala Ile Glu Ala Ala Val Lys Leu Ser Asn Arg Tyr Val Ser Asp
            370                 375                 380
Arg Phe Leu Pro Asp Lys Ala Ile Asp Leu Ile Asp Glu Ala Ser Ser
385                 390                 395                 400
Lys Val Arg Leu Lys Ser His Thr Thr Pro Asn Asn Leu Lys Glu Ile
                405                 410                 415
Glu Gln Glu Ile Glu Lys Val Lys Asn Glu Lys Asp Ala Ala Val His
                420                 425                 430
Ala Gln Glu Phe Glu Asn Ala Ala Asn Leu Arg Asp Lys Gln Thr Lys
            435                 440                 445
Leu Glu Lys Gln Tyr Glu Glu Ala Lys Asn Glu Trp Lys Asn Ala Gln
        450                 455                 460
Asn Gly Met Ser Thr Ser Leu Ser Glu Glu Asp Ile Ala Glu Val Ile
465                 470                 475                 480
Ala Gly Trp Thr Gly Ile Pro Leu Thr Lys Ile Asn Glu Thr Glu Ser
                485                 490                 495
Glu Lys Leu Leu Ser Leu Glu Asp Thr Leu His Glu Arg Val Ile Gly
                500                 505                 510
Gln Lys Asp Ala Val Asn Ser Ile Ser Lys Ala Val Arg Arg Ala Arg
            515                 520                 525
Ala Gly Leu Lys Asp Pro Lys Arg Pro Ile Gly Ser Phe Ile Phe Leu
        530                 535                 540
Gly Pro Thr Gly Val Gly Lys Thr Glu Leu Ala Arg Ala Leu Ala Glu
545                 550                 555                 560
Ser Met Phe Gly Asp Asp Ala Met Ile Arg Val Asp Met Ser Glu
                565                 570                 575
Phe Met Glu Lys His Ala Val Ser Arg Leu Val Gly Ala Pro Pro Gly
                580                 585                 590
Tyr Val Gly His Asp Asp Gly Gly Gln Leu Thr Glu Lys Val Arg Arg
            595                 600                 605
Lys Pro Tyr Ser Val Ile Leu Phe Asp Glu Ile Glu Lys Ala His Pro
        610                 615                 620
Asp Val Phe Asn Ile Leu Leu Gln Val Leu Asp Asp Gly His Leu Thr
625                 630                 635                 640
Asp Thr Lys Gly Arg Thr Val Asp Phe Arg Asn Thr Ile Ile Met
                645                 650                 655
Thr Ser Asn Val Gly Ala Gln Glu Leu Gln Asp Gln Arg Phe Ala Gly
                660                 665                 670
Phe Gly Gly Ser Ser Asp Gly Gln Asp Tyr Glu Thr Ile Arg Lys Thr
            675                 680                 685
Met Leu Lys Glu Leu Lys Asn Ser Phe Arg Pro Glu Phe Leu Asn Arg
        690                 695                 700
Val Asp Asp Ile Ile Val Phe His Lys Leu Thr Lys Glu Glu Leu Lys
705                 710                 715                 720
Glu Ile Val Thr Met Met Val Asn Lys Leu Thr Asn Arg Leu Ser Glu
                725                 730                 735
```

```
Gln Asn Ile Asn Ile Ile Val Thr Asp Lys Ala Lys Asp Lys Ile Ala
            740                 745                 750

Glu Glu Gly Tyr Asp Pro Glu Tyr Gly Ala Arg Pro Leu Ile Arg Ala
        755                 760                 765

Ile Gln Lys Thr Ile Glu Asp Asn Leu Ser Glu Leu Ile Leu Asp Gly
    770                 775                 780

Asn Gln Ile Glu Gly Lys Lys Val Thr Val Asp His Asp Gly Lys Glu
785                 790                 795                 800

Phe Lys Tyr Asp Ile Ala Glu Gln Thr Ser Glu Thr Lys Thr Pro Ser
                805                 810                 815

Gln Ala Xaa Leu Xaa Asn Ser Pro Lys Gln Ile Lys Val Leu Gly Cys
            820                 825                 830

Phe Phe Ser Ser Ile Glu Leu Xaa Lys Phe Val Lys Val Ser Ile Asn
            835                 840                 845

Glu Thr Ile Xaa Xaa Asn Asn His Gln Arg Ile Val Lys Asn Tyr Met
    850                 855                 860

Xaa Gln
865

(2) INFORMATION FOR SEQ ID NO:3:

(i) SEQUENCE CHARACTERISTICS:
        (A) LENGTH: 2019 base pairs
        (B) TYPE: nucleic acid
        (C) STRANDEDNESS: double
        (D) TOPOLOGY: linear (xi) SEQUENCE DESCRIPTION: SEQ ID NO:3:

ATGAGTAATA AAAATGCACA AGCTAGTAAG TCAAATAATA CTCCAACTTT AGATAGTTTA      60

GCTCGTGACT TAACAGTCAT TGCCAAAGAC GGTACATTGA ATCCTGTTAT AGGACGTGAT     120

AAAGAAATTA CACGTGTAAT TGAAGTATTA AGTAGACGTA CGAAAAACAA TCCTGTACTT     180

ATTGGAGAGC CAGGTGTTGG TAAAACTGCT ATTGCTGAAG GTTTAGCGCA AGCCATAGTG     240

AATAATGAGG TACCAGAGAC ATTAAAAGAT AAGCGTGTTA TGTCTTTAGA TATGGGAACA     300

GTAGTTGCAG GTACTAAATA TCGTGGTGAA TTTGAAGAGC GTCTGAAAAA GGTTATGGAA     360

GAAATCCAAC AAGCAGGTAA TGTCATCCTA TTTATTGATG AGTTGCATAC TTTAGTTGGT     420

GCTGGTGGTG CTGAAGGTGC TATCGATGCT TCGAATATTT TGAAACCGGC ATTAGCACGT     480

GGTGAATTAC AATGTATTGG TGCTACTACA TTAGATGAAT ATCGCAAAAA TATTGAAAAA     540

GACGCGGCTT TAGAACGTCG TTTCCAACCT GTACAAGTTG ATGAACCTTC AGTAGTAGAT     600

ACAGTTGCTA TTTTAAAAGG ATTAAGAGAT CGTTACGAAG CACACCATCG TATTAATATT     660

TCAGACGAAG CTATTGAAGC AGCTGTTAAA TTAAGTAACA GATACGTTTC AGATCGTTTC     720

TTACCAGATA AAGCAATTGA TTTAATTGAT GAAGCAAGTT CTAAAGTAAG ACTTAAGAGT     780

CATACGACAC CTAATAATTT AAAAGAAATT GAACAAGAAA TTGAAAAAGT TAAAAATGAA     840

AAAGATGCCG CAGTACATGC TCAAGAGTTT GAAAATGCTG CTAACCTGCG TGATAAACAA     900

ACAAAACTTG AAAAGCAATA TGAAGAAGCT AAAAATGAAT GGAAGAATGC ACAAAATGGC     960

ATGTCAACTT CATTGTCAGA AGAAGATATT GCTGAAGTTA TTGCAGGATG GACAGGTATC    1020

CCATTAACTA AAATCAATGA AACAGAATCT GAAAAACTTC TTAGTCTAGA AGATACATTA    1080

CATGAGAGAG TTATTGGGCA AAAAGATGCT GTTAATTCAA TCAGTAAAGC GGTTAGACGT    1140

GCCCGTGCAG GGTTAAAAGA TCCTAAACGA CCAATTGGTA GCTTTATCTT CCTTGGACCA    1200
```

```
ACTGGTGTTG GTAAAACTGA ATTAGCTAGA GCTTTAGCTG AATCAATGTT TGGCGATGAT    1260

GATGCGATGA TCCGTGTAGA CATGAGTGAA TTTATGGAAA ACACGCAGT GAGCCGATTA    1320

GTTGGTGCTC CTCCAGGATA TGTTGGTCAT GATGATGGTG GACAATTAAC TGAAAAAGTT    1380

AGACGTAAAC CATATTCTGT AATTTTATTT GATGAAATTG AAAAAGCTCA TCCAGATGTA    1440

TTTAATATTC TATTACAAGT TTTAGATGAT GGACATTTGA CAGATACAAA AGGACGTACA    1500

GTTGATTTCA GAAATACAAT TATCATAATG ACATCAAACG TTGGGGCACA AGAATTACAA    1560

GATCAACGAT TTGCTGGATT CGGTGGTTCA AGTGATGGAC AAGATTATGA AACAATTCGA    1620

AAAACGATGT TAAAAGAATT AAAAAATTCA TTCCGTCCAG AATTTTTAAA CCGTGTAGAT    1680

GATATCATTG TATTCCATAA ACTAACAAAA GAAGAATTAA AAGAAATTGT AACAATGATG    1740

GTTAATAAAT TAACAAATCG ATTATCTGAA CAAAACATAA ATATTATTGT TACTGATAAA    1800

GCGAAAGACA AAATCGCAGA AGAAGGATAT GATCCAGAAT ATGGTGCAAG ACCATTAATT    1860

AGAGCGATAC AAAAAACTAT CGAAGATAAT TTAAGTGAAT TAATATTAGA TGGTAATCAA    1920

ATTGAAGGTA AGAAAGTTAC AGTAGATCAT GATGGTAAAG AGTTTAAATA TGACATTGCT    1980

GAACAAACTT CAGAAACTAA AACACCATCG CAAGCATAA                           2019

(2) INFORMATION FOR SEQ ID NO:4:

(i) SEQUENCE CHARACTERISTICS:
        (A) LENGTH: 672 amino acids
        (B) TYPE: amino acid
        (C) STRANDEDNESS: single
        (D) TOPOLOGY: linear (xi) SEQUENCE DESCRIPTION: SEQ ID NO:4:

Met Ser Asn Lys Asn Ala Gln Ala Ser Lys Ser Asn Asn Thr Pro Thr
1               5                   10                  15

Leu Asp Ser Leu Ala Arg Asp Leu Thr Val Ile Ala Lys Asp Gly Thr
            20                  25                  30

Leu Asp Pro Val Ile Gly Arg Asp Lys Glu Ile Thr Arg Val Ile Glu
        35                  40                  45

Val Leu Ser Arg Arg Thr Lys Asn Asn Pro Val Leu Ile Gly Glu Pro
    50                  55                  60

Gly Val Gly Lys Thr Ala Ile Ala Glu Gly Leu Ala Gln Ala Ile Val
65                  70                  75                  80

Asn Asn Glu Val Pro Glu Thr Leu Lys Asp Lys Arg Val Met Ser Leu
                85                  90                  95

Asp Met Gly Thr Val Val Ala Gly Thr Lys Tyr Arg Gly Glu Phe Glu
            100                 105                 110

Glu Arg Leu Lys Lys Val Met Glu Glu Ile Gln Gln Ala Gly Asn Val
        115                 120                 125

Ile Leu Phe Ile Asp Glu Leu His Thr Leu Val Gly Ala Gly Gly Ala
    130                 135                 140

Glu Gly Ala Ile Asp Ala Ser Asn Ile Leu Lys Pro Ala Leu Ala Arg
145                 150                 155                 160

Gly Glu Leu Gln Cys Ile Gly Ala Thr Thr Leu Asp Glu Tyr Arg Lys
                165                 170                 175

Asn Ile Glu Lys Asp Ala Ala Leu Glu Arg Arg Phe Gln Pro Val Gln
            180                 185                 190

Val Asp Glu Pro Ser Val Val Asp Thr Val Ala Ile Leu Lys Gly Leu
        195                 200                 205

Arg Asp Arg Tyr Glu Ala His His Arg Ile Asn Ile Ser Asp Glu Ala
```

-continued

```
            210                 215                 220
Ile Glu Ala Ala Val Lys Leu Ser Asn Arg Tyr Val Ser Asp Arg Phe
225                 230                 235                 240
Leu Pro Asp Lys Ala Ile Asp Leu Ile Asp Glu Ala Ser Ser Lys Val
                245                 250                 255
Arg Leu Lys Ser His Thr Thr Pro Asn Asn Leu Lys Glu Ile Glu Gln
                260                 265                 270
Glu Ile Glu Lys Val Lys Asn Glu Lys Asp Ala Ala Val His Ala Gln
                275                 280                 285
Glu Phe Glu Asn Ala Ala Asn Leu Arg Asp Lys Gln Thr Lys Leu Glu
                290                 295                 300
Lys Gln Tyr Glu Glu Ala Lys Asn Glu Trp Lys Asn Ala Gln Asn Gly
305                 310                 315                 320
Met Ser Thr Ser Leu Ser Glu Glu Asp Ile Ala Glu Val Ile Ala Gly
                325                 330                 335
Trp Thr Gly Ile Pro Leu Thr Lys Ile Asn Glu Thr Glu Ser Glu Lys
                340                 345                 350
Leu Leu Ser Leu Glu Asp Thr Leu His Glu Arg Val Ile Gly Gln Lys
                355                 360                 365
Asp Ala Val Asn Ser Ile Ser Lys Ala Val Arg Arg Ala Arg Ala Gly
                370                 375                 380
Leu Lys Asp Pro Lys Arg Pro Ile Gly Ser Phe Ile Phe Leu Gly Pro
385                 390                 395                 400
Thr Gly Val Gly Lys Thr Glu Leu Ala Arg Ala Leu Ala Glu Ser Met
                405                 410                 415
Phe Gly Asp Asp Asp Ala Met Ile Arg Val Asp Met Ser Glu Phe Met
                420                 425                 430
Glu Lys His Ala Val Ser Arg Leu Val Gly Ala Pro Pro Gly Tyr Val
                435                 440                 445
Gly His Asp Asp Gly Gly Gln Leu Thr Glu Lys Val Arg Arg Lys Pro
                450                 455                 460
Tyr Ser Val Ile Leu Phe Asp Glu Ile Glu Lys Ala His Pro Asp Val
465                 470                 475                 480
Phe Asn Ile Leu Leu Gln Val Leu Asp Asp Gly His Leu Thr Asp Thr
                485                 490                 495
Lys Gly Arg Thr Val Asp Phe Arg Asn Thr Ile Ile Met Thr Ser
                500                 505                 510
Asn Val Gly Ala Gln Glu Leu Gln Asp Gln Arg Phe Ala Gly Phe Gly
                515                 520                 525
Gly Ser Ser Asp Gly Gln Asp Tyr Glu Thr Ile Arg Lys Thr Met Leu
                530                 535                 540
Lys Glu Leu Lys Asn Ser Phe Arg Pro Glu Phe Leu Asn Arg Val Asp
545                 550                 555                 560
Asp Ile Ile Val Phe His Lys Leu Thr Lys Glu Glu Leu Lys Glu Ile
                565                 570                 575
Val Thr Met Met Val Asn Lys Leu Thr Asn Arg Leu Ser Glu Gln Asn
                580                 585                 590
Ile Asn Ile Ile Val Thr Asp Lys Ala Lys Asp Lys Ile Ala Glu Glu
                595                 600                 605
Gly Tyr Asp Pro Glu Tyr Gly Ala Arg Pro Leu Ile Arg Ala Ile Gln
                610                 615                 620
Lys Thr Ile Glu Asp Asn Leu Ser Glu Leu Ile Leu Asp Gly Asn Gln
625                 630                 635                 640
```

-continued

```
Ile Glu Gly Lys Lys Val Thr Val Asp His Asp Gly Lys Glu Phe Lys
                645             650                 655
Tyr Asp Ile Ala Glu Gln Thr Ser Glu Thr Lys Thr Pro Ser Gln Ala
            660             665                 670
```

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:5:

ATAGCAACTG TATCTACTAC TGAAGG                        26

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:6:

ATAGCAACTG TATCTACTAC TGAAGG                        26